US00PP26118P3

(12) United States Plant Patent
Franken-Bembenek

(10) Patent No.: US PP26,118 P3
(45) Date of Patent: Nov. 24, 2015

(54) ***PRUNUS* TREE ROOTSTOCK NAMED 'GI31817'**

(50) Latin Name: ***Prunus* hybrid**
Varietal Denomination: Gi31817

(71) Applicant: Consortium Deutsche Baumschulen GmbH, Ellerbek (DE)

(72) Inventor: Sabine Franken-Bembenek, Giessen (DE)

(73) Assignee: Consortium Deutscher Baumschulen GmbH, Ellerbek (DE)

( * ) Notice: Subject to any disclaimer, the term of this patent is extended or adjusted under 35 U.S.C. 154(b) by 49 days.

(21) Appl. No.: 13/987,521

(22) Filed: Aug. 1, 2013

(65) Prior Publication Data

US 2015/0040274 P1 Feb. 5, 2015

(51) Int. Cl.
*A01H 5/08* (2006.01)
*A01H 5/00* (2006.01)

(52) U.S. Cl.
USPC ..... Plt./183
CPC ..... *A01H 5/00* (2013.01)

(58) Field of Classification Search
USPC ..... Plt./183
CPC ..... A01H 5/085
See application file for complete search history.

*Primary Examiner* — Keith Robinson
(74) *Attorney, Agent, or Firm* — The Webb Law Firm

(57) ABSTRACT

A new and distinct *Prunus* hybrid plant used as a rootstock for cherries that induces precocity and flat branching of the grafted plant.

2 Drawing Sheets

Botanical classification: *Prunus* hybrid.
Varietal denomination: 'Gi31817'.

BACKGROUND OF THE INVENTION

The present invention comprises a new and distinct cultivar of *Prunus* hybrid used as a rootstock known by the varietal name 'Gi31817'. The new variety was discovered in Giessen, Germany in 1970. The new variety is the result of a planned breeding program between an unnamed *Prunus canescens* variety (female parent) and a mixture of pollen as the male parentage from several unnamed and presumably unpatented varieties of *Prunus avium*. The new variety has larger leaves, less leaf pubescence, stronger vigor, and induces stronger vigor of a grafted tree than its female parent. When compared to the varieties making up its male parentage, the new variety does not grow as upright and also induces less growth and higher precocity of a grafted tree. The purpose of the breeding program was to produce a series of size-controlling, productive, and precocious rootstocks for sweet cherries. The new variety has been trial and field tested and has been found to retain its distinctive characteristics and remain true to type through successive propagations.

The new variety is similar to *prunus* rootstock 'GI 148/2' (U.S. Plant Pat. No. 9,622) in its rootstock induction of precosity, rootstock induction of flat branching, and the absence of root suckers. The leaves of the new variety have a different appearance than those of 'GI 148/2'. Further, the vigor of a grafted tree on the new variety is much greater than on 'GI 148/2'.

DESCRIPTION OF THE DRAWINGS

The accompanying photographic drawings illustrate the new cultivar taken during the first vegetation period after in vitro propagation at a nursery in Oberdorlar, Germany, with the color being as nearly true as is possible with color illustrations of this type.

DESCRIPTION OF THE PLANT

Figure 1:
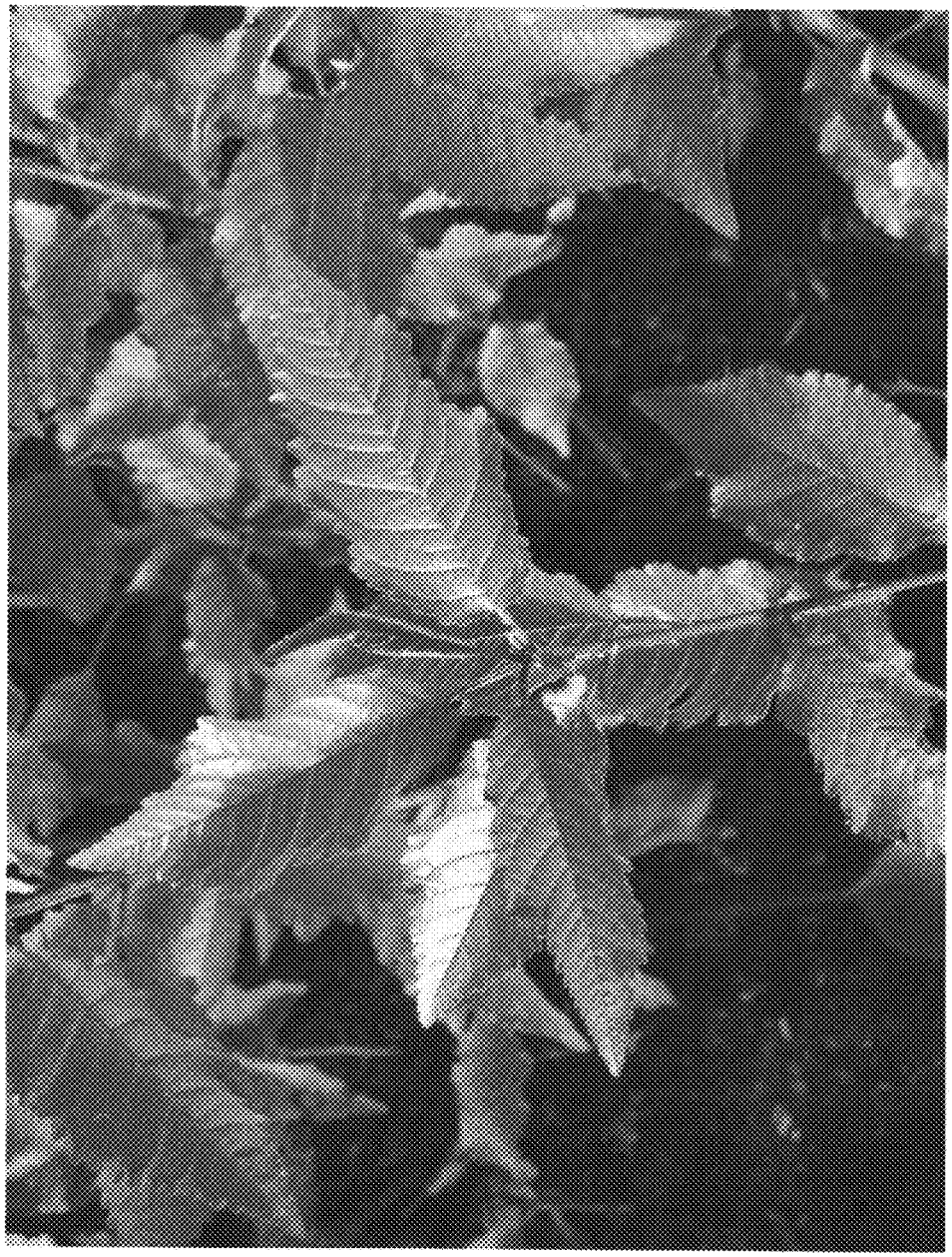
FIG. 1 is a close-up picture of the leaves and branches of the new variety.
Figure 2:
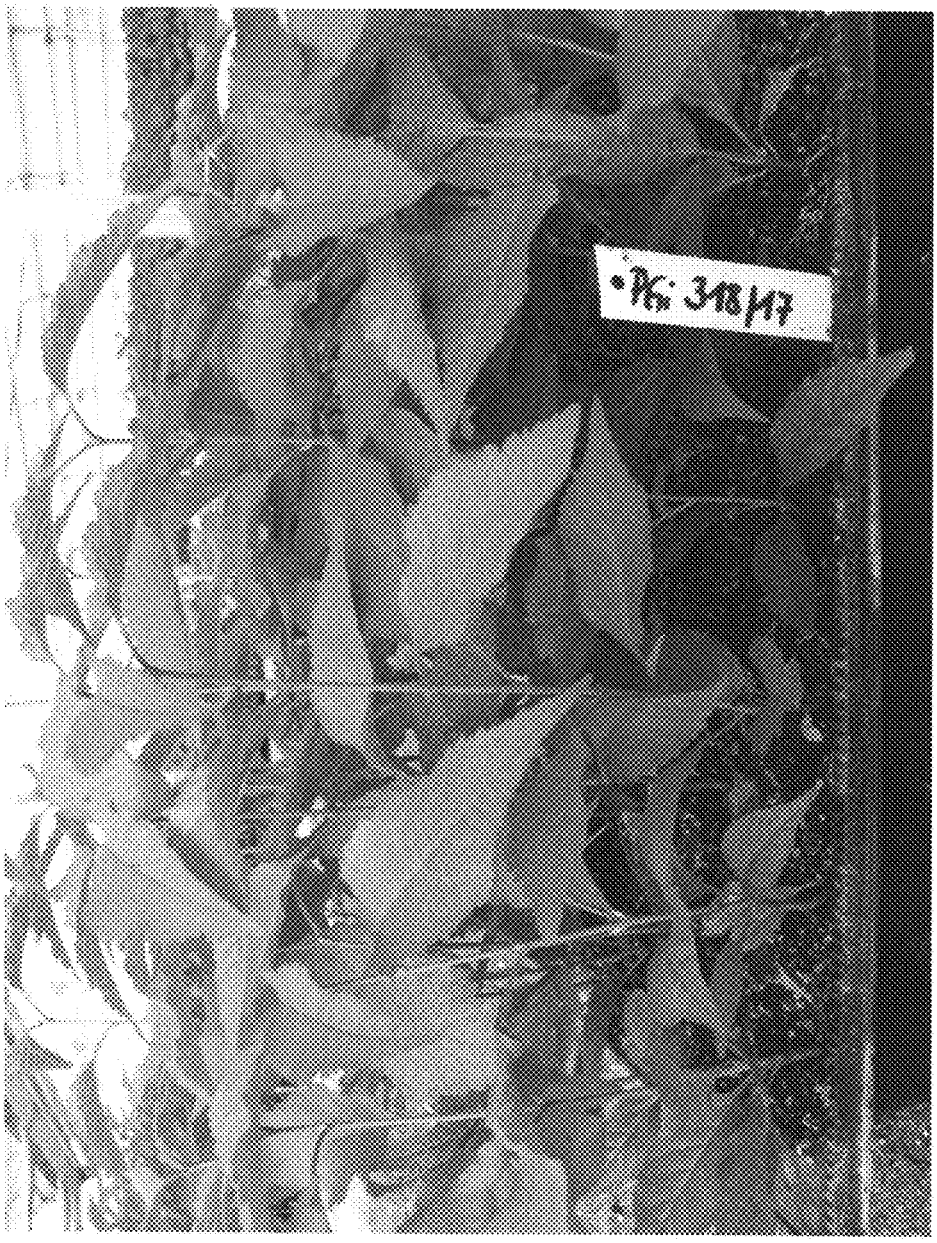
FIG. 2 is a picture of a numerous plants of the new variety.

The following detailed description sets forth the characteristics of the new cultivar. The data which defines these characteristics were collected by asexual reproduction carried by green cuttings under mist and in vitro conditions. The first asexual reproduction occurred in approximately 1975 in Giessen, Germany. The color readings were taken in natural daylight. Color references are primarily to The 2001 R.H.S. Colour Chart of The Royal Horticultural Society of London. Except where stated otherwise, the data collected for the description herein was taken on five-year old plants grown in an orchard under standard growing conditions in Witzenhausen-Wendershausen, Germany.

PLANT

Use: As a rootstock for sweet, sour, and ornamental cherries.
Fragrance: None observed.
Growth type: Semi-upright to upright.
Height: 360 cm five years after planting (in Giessen, German).
Spread: 310 cm five years after planting (in Giessen, Germany).
Pathogen resistance:
*Fungal disease*.—Tolerant to *Monilia laxa*.
*Viruses*.—Tolerant to ilarviruses PDV (prune dwarf virus) and PNRSV (*prunus necrotic* ringspot virus).

Trunk circumference: 88 mm two years after planting (in Giessen, Germany).
Trunk bark color: 175B.
Branches:
*Internode length*.—Medium.
*Diameter*.—Medium.
*Texture*.—Very weak pubescence.
*Color*.—175B.
Leaves:
*Length*.—Medium; 9 cm on long shoots, and 6 cm on spur shoots.
*Width*.—Medium; 4 cm on long shoots, and 3 cm on spur shoots.
*Form*.—Elliptic.
*Apex*.—Acute.
*Base*.—Obtuse.
*Margin*.—Serrate.
*Upper surface textures*.—Weakly glossy.
*Lower surface texture*.—Weak pubescence present.
*Venation pattern*.—Reticulate.
*Color*.—Upper surface: 137A. Lower surface: 137C.
*Petiole length*.—1.0 cm.
*Petiole texture*.—Weak pubescence present.
*Stipule length*.—Intermediate.
Flowers:
*Pedicel length*.—1.5 cm.
*Peduncle length*.—3.5 cm.
*Peduncle texture*.—Glabrous.
*Bud color*.—56D.
*Bloom timing*.—Similar to most sweet cherry cultivars, like 'Hedelfinger' (not patented).
*Shape*.—Round.
*Petals*.—Number: Five. Length: 0.8 cm. Width: 0.8 cm. Shape: Round. Color (fully opened): White on both surfaces.
*Sepals*.—Number: Five. Length: 0.4 cm. Diameter: 0.4 cm. Color: 144A.
*Pistil number*.—One.
Fruit shape: Elliptic.
Tree winter hardiness: Good; USDA Hardiness Zone of 6 to 7 (possibly 5b to 8a).
Performance as a grafted rootstock:
*Root sprouts*.—No suckers observed.
*Anchorage*.—Good.
*Compatibility*.—Good.
*Vigor*.—Reduces size of tree compared to *Prunus avium* rootstock, much more vigorous than 'GI 148/2', more vigorous than 'GI 148/1'.

I claim:

1. A new and distinct variety of *Prunus* hybrid plant used as rootstock as shown and described herein.

* * * * *